US 7,351,960 B2

(12) United States Patent
Belford

(10) Patent No.: US 7,351,960 B2
(45) Date of Patent: Apr. 1, 2008

(54) ENHANCED ION DESOLVATION FOR AN ION MOBILITY SPECTROMETRY DEVICE

(75) Inventor: Michael W. Belford, Santa Clara, CA (US)

(73) Assignee: Thermo Finnigan LLC, San Jose, CA (US)

( * ) Notice: Subject to any disclaimer, the term of this patent is extended or adjusted under 35 U.S.C. 154(b) by 91 days.

(21) Appl. No.: 11/131,072

(22) Filed: May 16, 2005

(65) Prior Publication Data

US 2006/0255264 A1 Nov. 16, 2006

(51) Int. Cl.
*H01J 49/04* (2006.01)

(52) U.S. Cl. .................... 250/288; 250/282; 250/290; 250/292; 250/291

(58) Field of Classification Search ............... 250/287, 250/288, 286, 282, 296
See application file for complete search history.

(56) References Cited

U.S. PATENT DOCUMENTS

| 4,977,320 | A | 12/1990 | Chowdhury et al. |
| 5,565,679 | A | 10/1996 | Tanner et al. |
| RE35,413 | E | 12/1996 | Mylchreest et al. |
| 5,905,258 | A | 5/1999 | Clemmer et al. |
| 6,248,999 | B1 | 6/2001 | Mylchreest et al. |
| 6,621,077 | B1 | 9/2003 | Guevremont et al. |
| 6,639,212 | B1 | 10/2003 | Guevremont et al. |
| 6,667,474 | B1* | 12/2003 | Abramson et al. .......... 250/288 |
| 6,753,522 | B2 | 6/2004 | Guevremont et al. |
| 6,770,875 | B1 | 8/2004 | Guevremont et al. |
| 6,774,360 | B2 | 8/2004 | Guevremont et al. |
| 6,787,765 | B2 | 9/2004 | Guevremont et al. |
| 6,799,355 | B2 | 10/2004 | Guevremont et al. |
| 6,822,224 | B2 | 11/2004 | Guevremont |
| 6,831,271 | B1 | 12/2004 | Guevremont et al. |
| 2001/0030285 | A1* | 10/2001 | Miller et al. ................ 250/288 |
| 2002/0185595 | A1 | 12/2002 | Smith et al. |
| 2003/0057367 | A1 | 3/2003 | Guevremont et al. |

(Continued)

FOREIGN PATENT DOCUMENTS

WO    WO 00/08454    2/2000

(Continued)

OTHER PUBLICATIONS

Counterman et al., "High-Order Structure and Dissociation of Gaseous Peptide Aggregates that are Hidden in Mass Spectra," J. Am. Soc. Mass Spectom., Elsevier Science Inc., vol. 9 (No. 8), p. 743-759, (1998).

(Continued)

*Primary Examiner*—Robert Kim
*Assistant Examiner*—Johnnie L Smith, II
(74) *Attorney, Agent, or Firm*—Charles B. Katz; David E. Allred

(57) ABSTRACT

An ion spectrometer apparatus is disclosed having an ion source, an ion mobility spectrometer device such as a FAIMS cell, and a capillary for transporting ions from the ion source to the entrance of the FAIMS cell. The capillary is heated to promote evaporation of solvent from incompletely desolvated droplets entering the capillary inlet, thereby preventing or minimizing operational problems associated with the presence of wet material in the FAIMS cell. The FAIMS cell may be used to selectively transmit ions to a mass analyzer.

19 Claims, 6 Drawing Sheets

U.S. PATENT DOCUMENTS

| | | | |
|---|---|---|---|
| 2004/0232326 A1 | 11/2004 | Guevremont et al. | |
| 2005/0092918 A1* | 5/2005 | Smith et al. | 250/288 |
| 2005/0167587 A1* | 8/2005 | Guevremont et al. | 250/294 |
| 2005/0178964 A1* | 8/2005 | Guevremont et al. | 250/294 |
| 2005/0258358 A1* | 11/2005 | Thakur | 250/288 |

FOREIGN PATENT DOCUMENTS

| | | |
|---|---|---|
| WO | WO 00/63949 | 10/2000 |
| WO | WO 03/067625 | 8/2003 |

OTHER PUBLICATIONS

Guevremont et al., "Combined Ion Mobility/Time-of-Flight Mass Spectrometry Study of Electrospray-Generated Ions," Anal. Chem., vol. 69 (No. 19), p. 3959-3965, (1997).

Kim et al., "Improved Ion Transmission from Atmospheric Pressure to High Vacuum Using a Multicapillary Inlet and Electrodynamic Ion Funnel Interface," Anal. Chem., vol. 72, p. 5014-5019, (2000).

* cited by examiner

ENHANCED ION DESOLVATION FOR AN ION MOBILITY SPECTROMETRY DEVICE

FIELD OF THE INVENTION

The present invention relates generally to ion mobility spectrometry, and more particularly to the desolvation of ions prior to introduction into a ion mobility spectrometry device, such as a high field asymmetric ion mobility spectrometry (FAIMS) cell.

BACKGROUND OF THE INVENTION

In ion mobility spectrometry devices, separation of gas-phase ions is accomplished by exploiting variations in ion drift velocities under an applied electric field arising from differences in ion mobilities. One well-known type of ion mobility spectrometry device is the FAIMS cell, which separates ions on the basis of a difference in the mobility of an ion at high field strength (commonly denoted as $K_h$) relative to the mobility of the ion at low field strength (commonly denoted as K). Briefly described, a FAIMS cell consists of a pair of spaced apart electrodes that define therebetween a separation region through which a stream of ions is directed. An asymmetric waveform comprising a high voltage component and a lower voltage component of opposite polarity, together with a DC voltage (referred to as the compensation voltage, or CV) is applied to one of the electrodes. When the ion stream contains several species of ions, only one ion species is selectively transmitted through the FAIMS cell for a given combination of asymmetric waveform peak voltage (referred to as the dispersion voltage, or DV) and CV. The remaining species of ions drift toward one of the electrode surfaces and are neutralized. The FAIMS cell may be operated in single ion detection mode, wherein the DV and CV are maintained at constant values, or alternatively the applied CV may be scanned with time to sequentially transmit ion species having different mobilities. FAIMS cells may be used for a variety of purposes, including to provide separation of an ion stream prior to entry into a mass analyzer. An example of this type of application is disclosed in U.S. Pat. No. 6,822,224 to Guevremont.

The performance of a FAIMS cell may be significantly compromised if liquid-phase material is admitted into the separation region. This condition may arise, for example, where the FAIMS cell is used in connection with an atmospheric pressure ionization source, such as an electrospray ionization source, in which a liquid solution of the analyte substance is introduced into the ionization chamber as a droplet spray. If the droplet desolvation process does not proceed to completion (which may tend to occur at high liquid flow rates), partially desolvated droplets may enter the FAIMS cell, causing several problems. First, the presence of the droplets may interfere with the separation of the ions, resulting in a loss of separation resolution (i.e., peak broadening). Second, the droplets may come into contact with the electrode surfaces, causing signal carry-over. Finally, accumulation of liquid on the electrodes will eventually cause the high-voltage asymmetric waveform to discharge, rendering the FAIMS cell inoperable.

A number of references in the prior art propose techniques for avoiding admission of liquid-phase material into the separation region of the FAIMS cell. Generally, these techniques involve providing a heated counter-flowing gas stream opposing the ion/droplet stream flow to promote desolvation of any residual droplets. Examples of this approach are described, for example, in PCT Application No. PCT/CA03/00173 (International Publication No. WO 03/067625) to Ionalytics Corporation. However, use of the counterflow gas approach carries several disadvantages. First, introduction of the counterflow gas significantly increases overall pumping requirements. Additionally, the flow rate of the counterflow gas must be carefully controlled, since inadequate or excessive flow rates can change the rate of ion transport through the FAIMS cell, in turn affecting the transmission of selected ion species. Still further, this approach may require special adaptation of one or both electrodes. Thus, there exists a need in the art for an enhanced desolvation technique for use with FAIMS cells that avoids the limitations of the counterflow gas approach.

SUMMARY

According to one embodiment of the invention, a mass spectrometer apparatus is provided that includes an ion source for generating analyte ions, an ion mobility spectrometry device having a plurality of electrodes and being operable to separate the analyte ions according to their mobilities, and at least one capillary for transporting the analyte ions from the ion source to the ion mobility spectrometry device. The capillary is heated to promote evaporation of any residual liquid solvent that enters the capillary inlet. The use of a heated capillary for droplet desolvation avoids the need to provide a counterflow gas and the associated disadvantages.

In accordance with specific embodiments of the invention, the capillary terminates in an outlet orifice that opens to a first reduced-pressure interface region. Ions leaving the capillary proceed into the separation region of a FAIMS cell. Selectively transmitted ions exit the FAIMS cell and pass into a second interface region, where they are focused and are transmitted through a skimmer orifice into a vacuum region. The ions may then be transported through one or more ion guides into a mass analyzer.

DETAILED DESCRIPTION OF EMBODIMENTS

Figure 1:
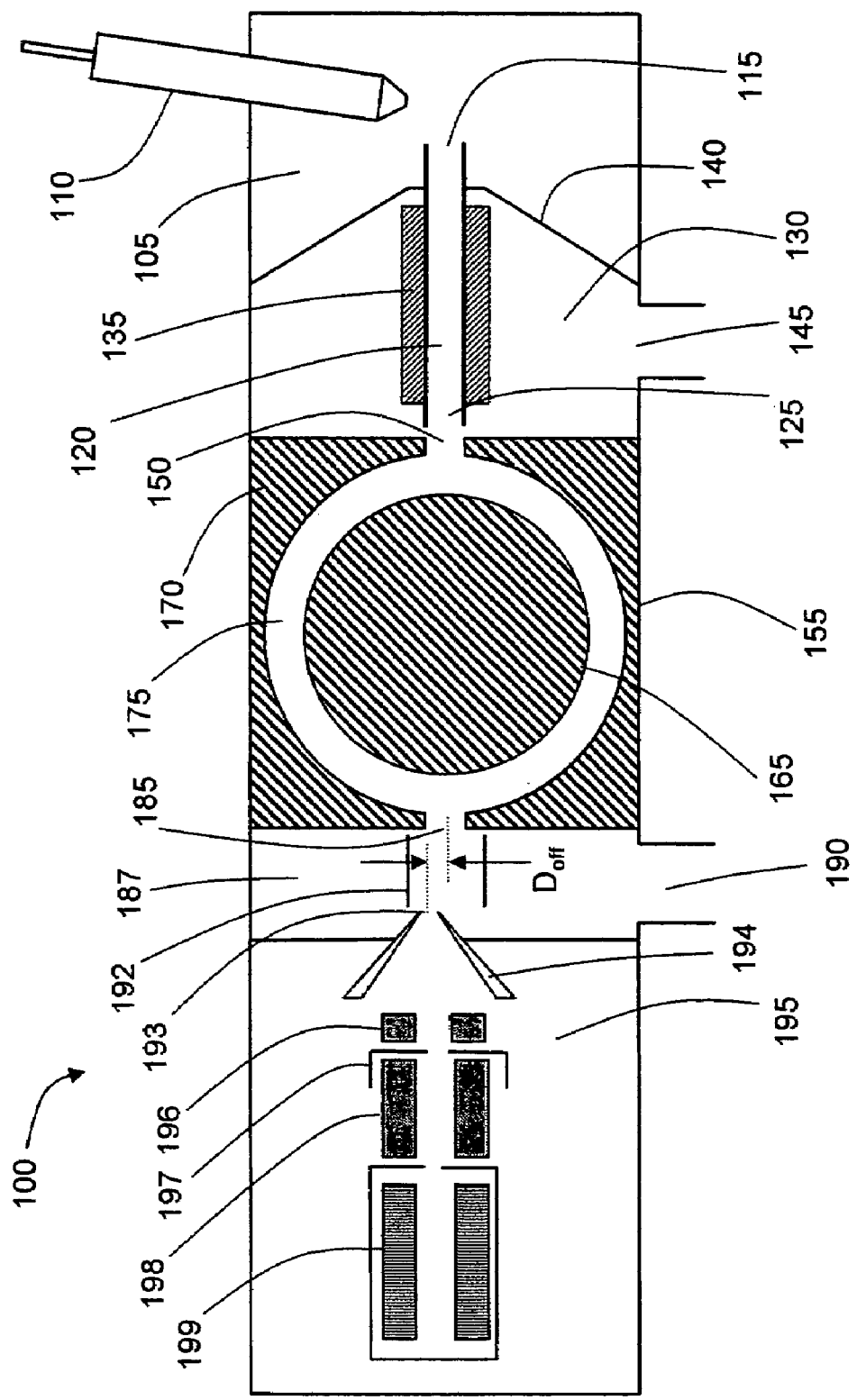
FIG. 1 is a symbolic diagram depicting a mass spectrometer apparatus in accordance with a first embodiment of the invention, the apparatus including an ion mobility device.

FIG. 1 symbolically depicts a mass spectrometer system 100 configured in accordance with a first embodiment of the invention. A solution of sample to be analyzed is introduced as a spray of liquid droplets into an ionization chamber 105 via probe 110. Ionization chamber 105 is maintained at a high pressure relative to the regions downstream in the ion path, typically at or near atmospheric pressure. Probe 110 may be configured as an electrospray ionization (ESI) probe, wherein a high DC voltage (either positive or negative) is applied to the capillary through which the sample solution flows. This voltage imparts a charge to the droplets as they are emitted from the capillary exit. The charge accumulates at the droplet surface during solvent evaporation, causing droplet fragmentation and the formation of analyte ions. Other suitable ionization techniques may be utilized in place of ESI, including without limitation such well-known techniques as atmospheric pressure chemical ionization (APCI), heated electrospray ionization (HESI), and thermospray ionization.

At least a portion of the analyte ions produced in ionization chamber 105 are drawn into an inlet orifice 115 of a capillary 120. Capillary 120 is an elongated tube extending from inlet orifice 115 to an outlet orifice 125, and has a typical inner diameter of between 250 and 700 µm. The capillary tube may be formed from a metallic material such as stainless steel. Use of an electrically conductive material allows an offset voltage to be applied to capillary 120 to develop electric fields that urge ions into and through the capillary. Alternatively, a non-metallic material such as quartz may be employed to construct capillary 120. Inlet orifice 115 opens to ionization chamber 105, and outlet orifice opens to a reduced-pressure interface region 130, which is typically maintained at a pressure of approximately 100 torr, although this pressure will vary significantly with changes in operating parameters such as flow rates. At least a portion of capillary 120 is surrounded by and in good thermal contact with a heat source, such as jacket heater 135. Jacket heater 135, which may take the form of a conventional resistance heater, is operable to raise the temperature of capillary 120 to promote desolvation of droplets entering capillary 120, as described below. Reduced-pressure interface region 130 is divided from ionization chamber 105 by partition 140, and is evacuated by a mechanical pump via vacuum port 145.

At high sample solution flow rate conditions, the residence time within ionization chamber 105 will typically be inadequate for complete desolvation of all droplets. Consequently, the ion stream entering inlet orifice 115 will be accompanied by partially desolvated droplets. As discussed above, the introduction of liquid material into a FAIMS cell or other ion mobility device may have significant deleterious effects on its performance. To avoid these problems, capillary 120 is heated to a temperature sufficient to cause substantially all of the residual solvent to evaporate as the droplets are transported through capillary 120. The temperature required for complete evaporation will depend on parameters of capillary length, flow rate, solvent volatility, and solvent concentration. Under usual conditions, jacket heater 135 is operated to maintain the temperature of the capillary within the range of 350-400° C.; however, temperatures in excess of 500° C. may be necessary to achieve complete evaporation. Preferably, the operation of jacket heater 135 may be controlled via user input so as to ensure that the capillary temperature is maintained at an operationally optimal value.

Analyte ions, together with solvent vapor and neutral gas molecules (which are present in relatively large quantities in ionization chamber 105 when nebulizing and/or supplemental gas streams are employed to assist the droplet formation process), are transported through capillary 120 under the influence of the pressure gradient (and, optionally, an electric field), and emerge from outlet orifice 125 into reduced pressure region 130. Outlet orifice 125 is positioned adjacent entrance orifice 150 of FAIMS cell 155 to facilitate transmission of ions into FAIMS cell 155. As will be discussed below in connection with FIG. 5, a small chamber (not depicted in FIG. 1) is disposed proximally to entrance orifice 150 to allow for the introduction of a carrier gas flow that assists in transporting ions through FAIMS cell 155. Entrance orifice 150 has a typical diameter of about 1 mm.

The principles of the design and operation of FAIMS cells and other ion mobility spectrometry devices have been extensively described elsewhere in the art (see, for example, U.S. Pat. No. 6,639,212 to Guevremont et al.), and hence will not be described in detail herein. Generally speaking, FAIMS cell 155 includes inner and outer electrodes 165 and 170 having radially opposed surfaces, which define therebetween an annular separation region 175 through which the ions are transported. The FAIMS cell geometry depicted in FIGS. 1-4 (referred to in the art as a "side-to-side FAIMS cell"), in which the longitudinal axes (directed out of the page) of inner electrodes 165 and outer electrode 170 are oriented transversely with respect to the overall direction of ion flow, is presented by way of a non-limiting example; other FAIMS cell geometries, including spherical geometries (comprising inner and outer electrodes having radially opposed spherical or spheroidal surfaces) as well as those geometries discussed below in connection with FIG. 6, are regarded as being within the scope of the present invention. Ion separation is effected within separation region 175 by applying an asymmetric waveform having a peak voltage DV and a compensation voltage CV to one of the inner or outer electrodes. The values of CV and DV are set to allow transmission of a selected ion species through separation region 175. Other ion species having different relative values of high field and low field mobilities will migrate to the surface of one of the electrodes and be neutralized. As alluded to above, the values of CV and DV may be maintained constant for single ion monitoring, or CV may be scanned over time to enable analysis of multiple ion species.

It should be further noted that the present invention should not be construed as limited to use with a FAIMS cell, but instead may be implemented in connection with any device that exploits variations in ion mobilities to achieve separation between different ion species.

The selected ions emerge from FAIMS cell 155 through an exit orifice 185 into a second interface region 187. Exit orifice 185 has a typical diameter of about 1 mm. Second interface region 187 is evacuated via vacuum port 190 to a pressure of approximately 1 torr (again, this pressure may vary considerably depending on operating parameters and instrument configuration) The ions leaving FAIMS cell 155 are focused by tube lens 192 (or other suitable ion optics) and are transferred through an orifice 193 of a skimmer 194 into a vacuum region 195 maintained at a low pressure (typically around 100 millitorr) relative to second interface region 187. Vacuum region 195 will typically be evacuated by turbo or similar pumps via a vacuum port (not depicted). Skimmer 194 may be fabricated from an electrically conductive material, and an offset voltage may be applied to skimmer 194 to assist in the transport of ions through interface region and into skimmer orifice 193. Ions passing through skimmer orifice 193 may be focused by a short quadrupole rod set 196 for transmission through an electrostatic lens 197. An ion guide 198, which may take the form of a quadrupole or octapole rod set, transports the ions to an analyzer 199 for mass analysis. Analyzer 199 may be implemented as any one or a combination of conventional mass analyzers, including (without limitation) a quadrupole mass analyzer, ion trap, or time-of-flight analyzer. Without restricting the present invention to any particular form of mass analyzer or method of use thereof, analyzer 199 may also be operable to provide MS" analysis, wherein the ions are deliberately fragmented and a mass analysis is performed on the fragment ions.

As a safeguard against transport of droplets and/or other condensed phase material into vacuum region 195, which could result in contamination of mass analyzer 199 and consequent malfunction, the ion flow axis of skimmer orifice 193 may be laterally offset with respect to the ion flow axes of FAIMS cell exit orifice 185 so that no line-of-sight flight path exists from the FAIMS cell 155 to analyzer 199. Droplets moving through second interface region 187 are undeflected (or deflected by a lesser degree relative to ions) by the electric field created by the voltages applied to skimmer 194 and/or other conductive surfaces, and will thus impact the solid surfaces of skimmer 194 rather than pass through orifice 193. For a typical application, the offset distance (indicated as Doff in FIG. 1) will be approximately 0.060-0.080 inches.

Figure 2:
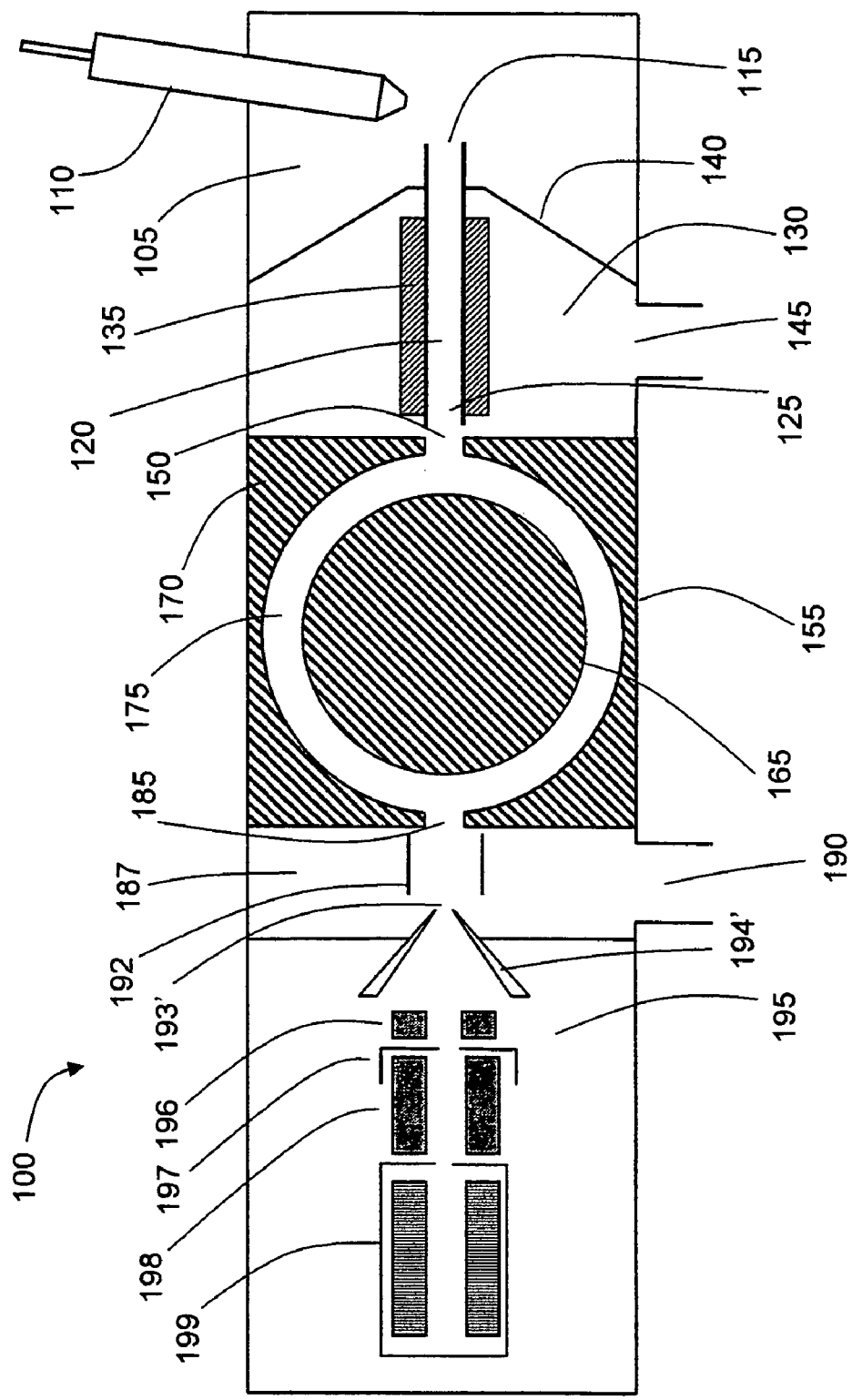
FIG. 2 is a symbolic diagram depicting a variation of the mass spectrometer apparatus of FIG. 1, the difference being the alignment of the skimmer ion flow axis with the axes defined by the ion mobility device and the capillary.
Figure 3:
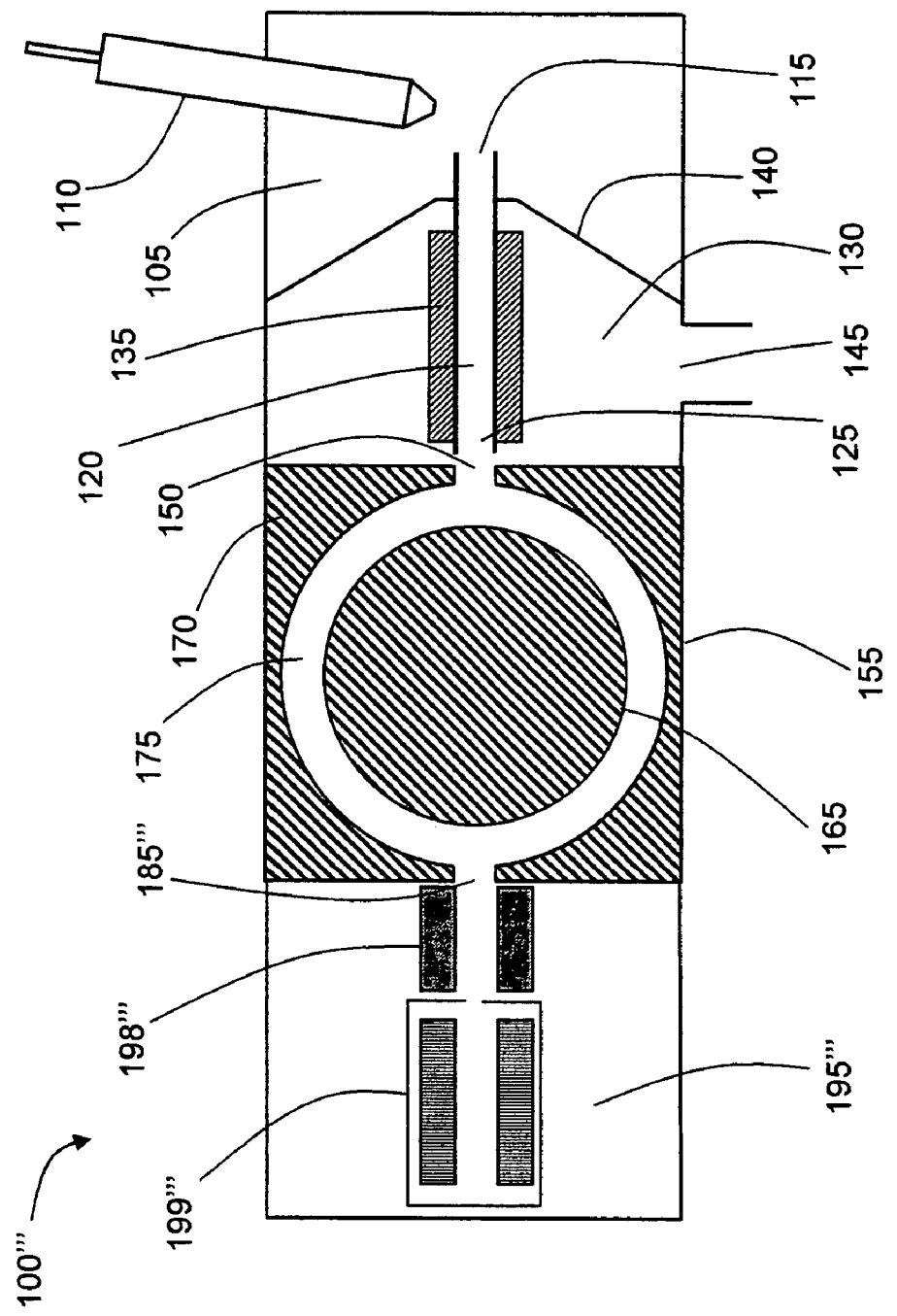
FIG. 3 is a symbolic diagram depicting a mass spectrometer apparatus in accordance with a second embodiment of the invention, which omits the skimmer and tube lens and includes an ion mobility device having an exit opening to a vacuum region.
Figure 4:
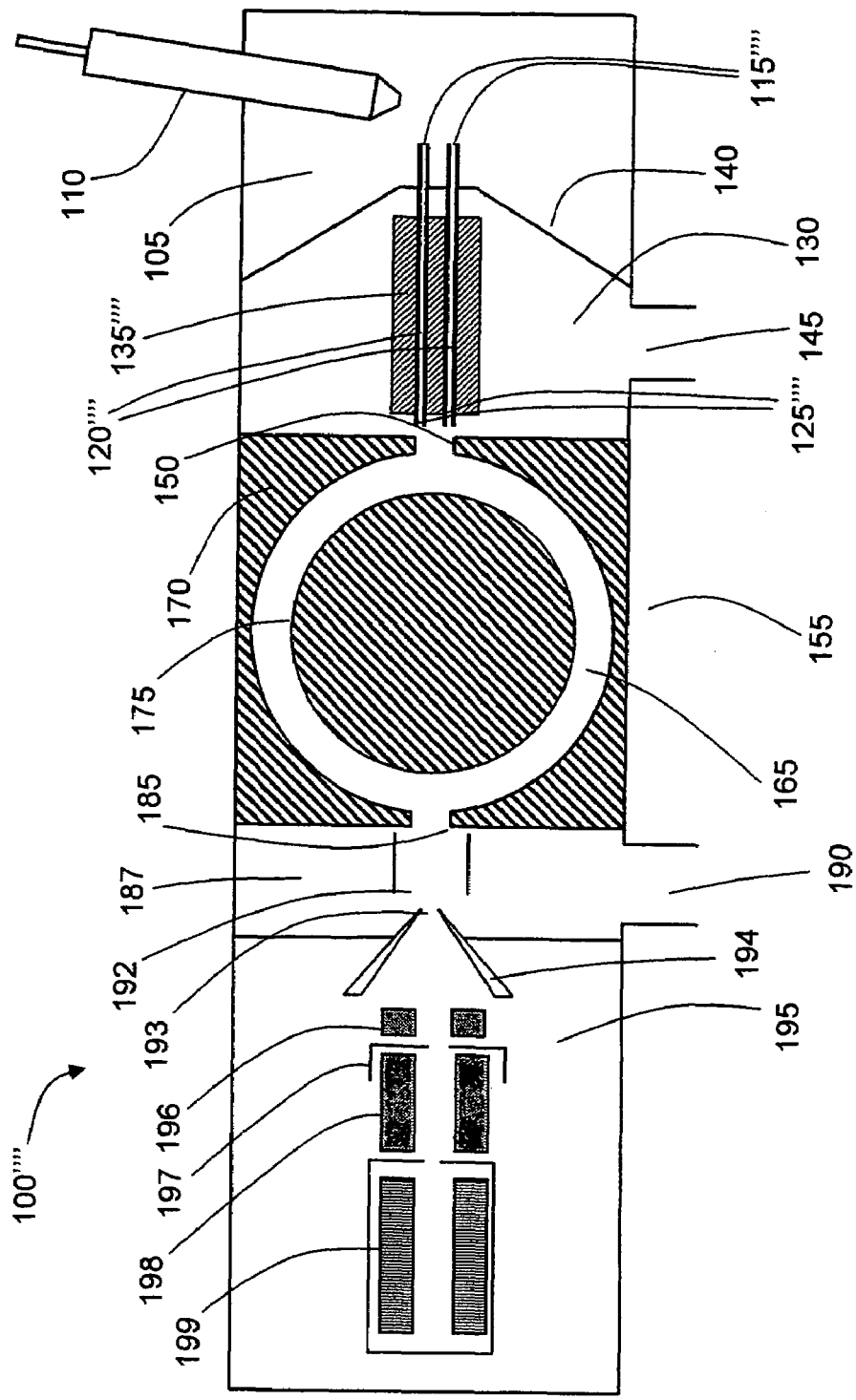
FIG. 4 is a symbolic diagram depicting a mass spectrometer apparatus in accordance with a third embodiment of the invention, wherein multiple capillaries are utilized to transport sample ions from the ion source to the ion mobility device.

FIGS. 2-4 depict various alternative embodiments of the mass spectrometer system 100 depicted in FIG. 1 and described above. Referring to FIG. 2, mass spectrometer system 100' is closely similar to mass spectrometer 100 and includes the same components, the distinction being that skimmer 194' is positioned such that the ion flow axis of orifice 193' is substantially co-linear with the ion flow axis of FAIMS cell exit orifice 185. This design lacks the protection against droplet entry into the vacuum region afforded by the offset axes configuration of the FIG. 1 embodiment, but may provide enhanced ion transmission since no turning of the ion flow is required.

In the FIG. 3 embodiment, mass spectrometer system 100''' is configured such that exit orifice 185''' of FAIMS cell 155''' opens directly to vacuum region 195'''. This embodiment omits the tube lens, skimmer, short quadrupole rod set, and second interface region of FIG. 1. Ions emerging from exit orifice 185''' are transported and focused by quadrupole rod set 198''' into mass analyzer 199'''. The omission of the second interface region and associated components may improve overall ion transmission and reduce system cost. However, the pump loading for the vacuum pump(s) that evacuate vacuum region 195''' will be greater relative to the FIG. 1 embodiment.

The FIG. 4 embodiment is closely similar to the embodiment of FIG. 1, the difference being the use of multiple heated capillaries 120'''' to transport ions from ionization chamber 105 to reduced pressure region 130 in place of the single capillary 120 of the FIG. 1 embodiment. The number and size (inner diameter) of capillaries 120'''' will depend on considerations of flow rates and pumping requirements. Capillaries 120'''' may be distributed radially about a central point, or may alternatively be arranged in other geometries, such as in a rectilinear array. A heater 135'''', placed in thermal contact with capillaries 120'''', controls the temperature of the capillaries to a desire setpoint. Heater 135'''' may take the form of a unitary structure having a set of bores, with each bore receiving a respective capillary; alternatively, heater 135'''' may be implemented as multiple individual heaters, each heater being associated with and controlling the temperature of a corresponding capillary.

Figure 5:
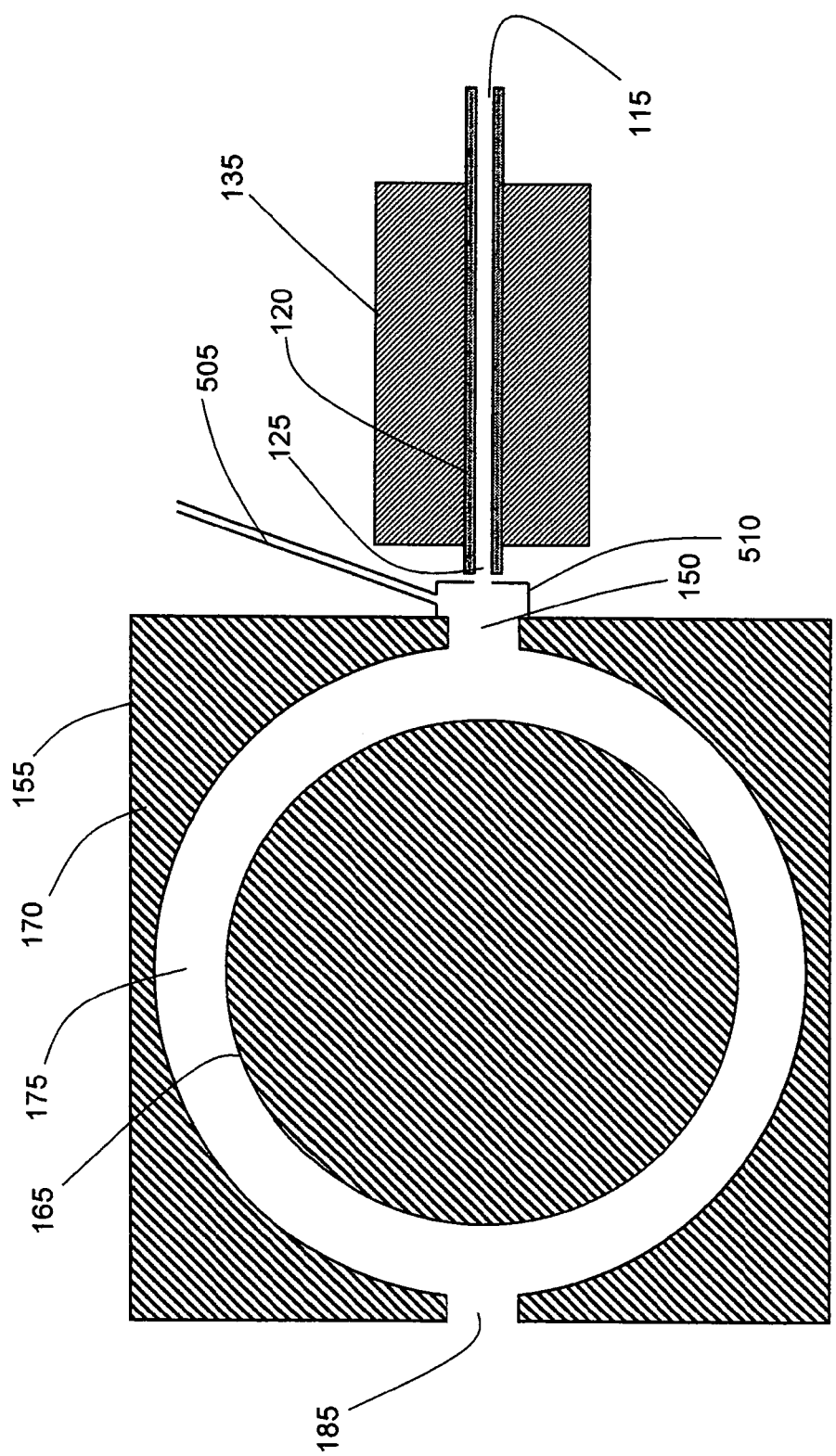
FIG. 5 is a symbolic diagram depicting a portion of the mass spectrometer apparatus of FIGS. 1-4, showing in particular structures at the entrance of the ion mobility device for introducing sample ions and gas into the analyzer region of the device.

FIG. 5 depicts in greater detail the entrance region of FAIMS cell 155. As described above in connection with FIG. 1, ions emerging from outlet orifice 125 of capillary 115 are entrained by a carrier gas flow to effect the controlled transport of ions through the separation region 175. The carrier gas, typically helium or other inert gas, is introduced via a conduit 505 and combines with the analyte ions in chamber 510. The combined ion/carrier gas flow then enters FAIMS cell 155 through entrance orifice 150. The carrier gas flow is carefully metered to maintain flow rates within predetermined limits. The carrier gas flow rates will depend on the FAIMS cell size, electrode geometry, and operational considerations; in a typical commercial instrument implementation, the carrier gas flow rate may be approximately 1 liter/minute.

Figure 6A:
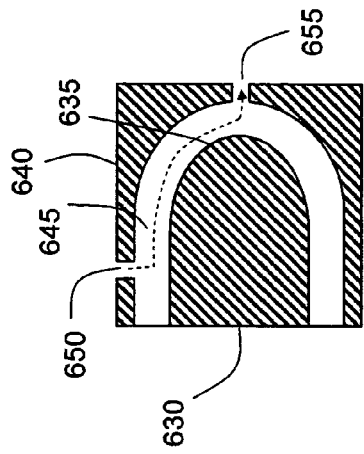
FIGS. 6(a)-6(d) are symbolic diagrams depicting exemplary configurations of electrodes in the ion mobility device.
Figure 6C:
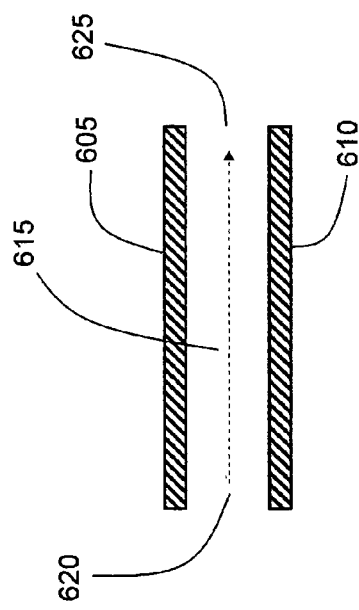
Figure 6B:
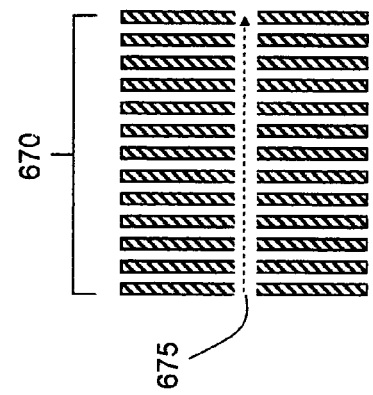
Figure 6D:
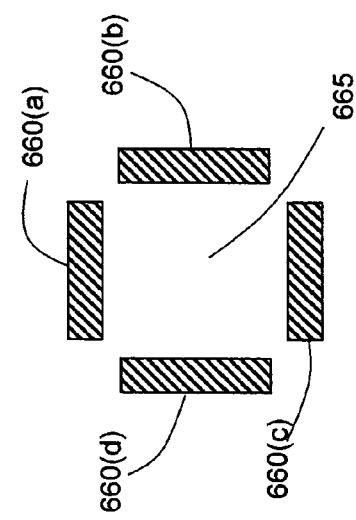

FIGS. 6(a)-(d) present examples of alternative electrode geometries known in the art for use in FAIMS cells or other ion mobility spectrometry devices. FIG. 6(a) depicts a simple FAIMS cell electrode geometry comprising two parallel flat plate electrodes 605 and 610, which define therebetween a separation region 615. Ions enter separation region 615 via end 620 and have a primary flow axis parallel to the plates. The selectively transmitted ions leave the FAIMS cell through the opposite end 625. FIG. 6(b) depicts a more complex FAIMS cell electrode geometry, referred to in the art as a "domed" FAIMS cell and described in U.S. Pat. No. 6,787,765 to Guevremont et al., comprising an inner cylindrical electrode 630 having a domed end portion 635 that is positioned inside a complementarily-shaped outer electrode 640. Ions enter separation region 645 through an inlet orifice 650, and travel along the indicated path such that the selectively transmitted ions leave the separation region through outlet orifice 655. FIG. 6(c) depicts an end view of yet another FAIMS cell geometry, comprising four multipole electrodes 660(a)-(d) arranged in rectilinear fashion to define a separation region 665. Ions travel in a direction perpendicular to the drawing plane from an entrance end to an exit end. Finally, FIG. 6(d) depicts a plurality of lens stack electrodes (collectively denoted as 670) used for a conventional (non-FAIMS) ion mobility spectrometry device. Lens stack electrodes 670 define a channel 675 through which ions pass. Voltages of progressively increasing magnitude (in the direction of ion travel) are applied to the lens stack electrodes to generate an electric field. The velocity at which ions pass through channel 675, which holds a bath gas maintained at or around atmospheric pressure, is determined by their mobilities such that ions having different mobilities are separated. It should be noted that the foregoing examples are intended as being illustrative rather than limiting the invention.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

What is claimed is:

1. Mass spectrometer apparatus, comprising:
   an ion source for generating analyte ions;

high field asymmetric ion mobility spectrometry (FAIMS) cell having a plurality of electrodes, the FAIMS cell being operable to separate analyte ions according to their ion mobilities; and at least one elongated capillary for transporting the analyte ions from the ion source to the FAIMS cell, the capillary being heated to evaporate at least some of a solvent admitted into the capillary; and wherein:
the capillary has an inlet orifice opening to a first region and an outlet orifice opening to a second region;
an entrance of the FAIMS cell opens to the second region; and
the first region is maintained at a significantly higher pressure relative to the second region.

2. The apparatus of claim 1, wherein the second region, is maintained at a pressure of approximately 100 Torr.

3. The apparatus of claim 1, wherein the capillary is heated to a temperature in the range of 200-500° C.

4. The apparatus of claim 2, wherein the FAIMS cell has an entrance orifice opening to the second region and an exit orifice opening to a third region, the third region being maintained at a reduced pressure relative to the second region.

5. The apparatus of claim 4, further comprising ion optics for transporting to a mass analyzer at least a portion of the ions that pass though the exit orifice, the ion optics being located in a vacuum region maintained at a reduced pressure relative to the third region, and a skimmer disposed between the exit orifice and the ion optics for admitting analyte ions into the vacuum region though a skimmer orifice.

6. The apparatus of claim 5, wherein an ion flow axis defined by the skimmer orifice is offset from an ion flow axis defined by an exit orifice of the FAIMS cell.

7. The apparatus of claim 5, further comprising a tube lens disposed between the exit orifice and the skimmer for focusing analyte ions to a flow centerline.

8. The apparatus of claim 2, wherein the FAIMS cell has an entrance orifice opening to the second region and an exit orifice opening to a vacuum region, the vacuum region being maintained at a reduced pressure relative to the second region, and further comprising a quadrupole ion guide disposed in the vacuum region for transporting at least a portion of ions passing through the ion exit to a mass analyzer.

9. The apparatus of claim 1, wherein the at least one capillary includes a plurality of capillaries, each transporting a portion of the analyte ions and each being heated to evaporate at least some of the solvent admitted into the capillary.

10. The apparatus of claim 1, wherein the FAIMS cell comprises first and second electrodes having radially opposed spherical or cylindrical surfaces.

11. The apparatus of claim 1, wherein the ion source comprises an electrospray ion source.

12. A mass spectrometer system, comprising:
an ion source for generating analyte ions by generating a spray of droplets of analyte in association with a solvent;
a FAIMS cell comprising at least two electrodes defining a separation region, wherein the two electrodes have radially opposed spherical or cylindrical surfaces;
at least one elongated capillary for transporting the analyte ions from the ion source to the FAIMS cell, the capillary being heated to evaporate at least some of a solvent admitted into the capillary; and
a mass analyzer for mass analyzing ions selectively transmitted by the FAIMS cell.

13. The system of claim 12, wherein the capillary has an inlet orifice opening to a first region and an outlet orifice opening to a second region, the first region being maintained at a significantly higher pressure relative to the second region.

14. The system of claim 12, wherein the capillary is heated to a temperature in the range of 200-500° C.

15. The system of claim 13, wherein the FAIMS cell has an entrance orifice opening to the second region and an exit orifice opening to a third region, the third region being maintained at a reduced pressure relative to the second region.

16. The system of claim 12, wherein an ion flow axis defined by the skimmer orifice is offset from an ion flow axis defined by an exit orifice of the FAIMS cell.

17. The system of claim 12, wherein the at least one capillary includes a plurality of capillaries, each transporting a portion of the analyte ions and each being heated to evaporate at least some of the solvent admitted into the capillary.

18. The system of claim 12, wherein the mass analyzer comprises an ion trap.

19. The system of claim 12, wherein the mass analyzer comprises a time-of-flight analyzer.

* * * * *